United States Patent [19]

Fay et al.

[11] Patent Number: 4,859,063
[45] Date of Patent: Aug. 22, 1989

[54] IMAGING MICROSPECTROFLUORIMETER

[75] Inventors: Fredric S. Fay; Kevin E. Fogarty, both of Worcester; Cyril Rodgers, Paxton, all of Mass.

[73] Assignee: University of Massachusetts Medical Center, Worcester, Mass.

[21] Appl. No.: 204,931

[22] Filed: May 31, 1988

Related U.S. Application Data

[63] Continuation of Ser. No. 34,777, Apr. 3, 1987, abandoned, which is a continuation-in-part of Ser. No. 900,407, Aug. 26, 1986, Pat. No. 4,744,667, which is a continuation-in-part of Ser. No. 828,766, Feb. 11, 1986, abandoned.

[51] Int. Cl.$^4$ ............................................. G01N 21/64
[52] U.S. Cl. ................................. 356/418; 250/458.1; 358/42; 358/227
[58] Field of Search ............... 356/414, 416, 417, 418; 350/521; 250/458.1, 459.1, 461.1, 461.2; 358/42, 227; 382/6

[56] References Cited

U.S. PATENT DOCUMENTS

| | | | |
|---|---|---|---|
| 3,913,128 | 10/1975 | Van den Bosch | 358/42 |
| 3,973,725 | 8/1976 | Watanabe et al. | 356/39 |
| 4,125,828 | 11/1978 | Resnick et al. | 250/461.2 |
| 4,191,940 | 3/1980 | Polcyn et al. | 250/226 |
| 4,364,630 | 12/1982 | Hayasaka | 350/521 |
| 4,443,108 | 4/1984 | Webster | 350/315 |
| 4,524,383 | 6/1985 | de Rooij | 358/55 |
| 4,573,195 | 2/1986 | de France | 382/6 |
| 4,661,986 | 4/1987 | Adelson | 382/41 |
| 4,744,667 | 5/1988 | Fay et al. | 356/417 |

FOREIGN PATENT DOCUMENTS

| | | |
|---|---|---|
| 1019841 | 11/1957 | Fed. Rep. of Germany. |
| 2316386 | 10/1974 | Fed. Rep. of Germany. |
| 0010035 | 4/1968 | Japan. |

OTHER PUBLICATIONS

F. S. Fay, K. E. Fogarty, J. M. Coggins, Analysis of Molecular Distribution in Single Cells Using a Digital Imaging Microscope, *Optical Methods in Cell Physiology*, P. DeWeer and B. Salzberg, eds., John Wiley & Sons, (New York), 1985.

F. S. Fay, K. Fujiwara, D. D. Rees and K. E. Fogarty, Distribution of α—Actinin in Single Isolated Smooth Muscle Cells, *The Journal of Cell Biology*, vol. 96, Mar. 1983, pp. 783–795.

D. A. Williams, K. E. Fogarty, R. Y. Tsien and F. S. Fay, Calcium Gradients in Single Smooth Muscle Cells Revealed by the Digital Imaging Microscope Using Fura-2, *Nature*, vol. 318, No. 6046, pp. 558–561, 12 Dec. 1985.

Chance et al., "A Time Sharing Fluorometer for the Readout of Intracellular Oxidation–Reduction States of NADH and Flavoprotein" *The Review of Scientific Instruments*, vol. 42, No. 7, Jul. 1979, pp. 951–957.

Zeidler, "The Fluorescence Microscope," *Laboratory Equipment Digest*, vol. 12, No. 7, Jul. 1974, pp. 48, 50–54, 56, 57.

*Primary Examiner*—F. L. Evans
*Attorney, Agent, or Firm*—Hamilton, Brook, Smith & Reynolds

[57] ABSTRACT

A microscope is modified to allow for precise imaging of samples using different filters at different focal planes under computer control. A filter accessory includes a filter disc having bandpass filters. The filter disc may be rotated to move a selected filter into the optical path between a light source and the microscope sample. Adjustment of the image plane of the microscope is controlled by the computer using feedback from a lens position sensor.

15 Claims, 18 Drawing Sheets

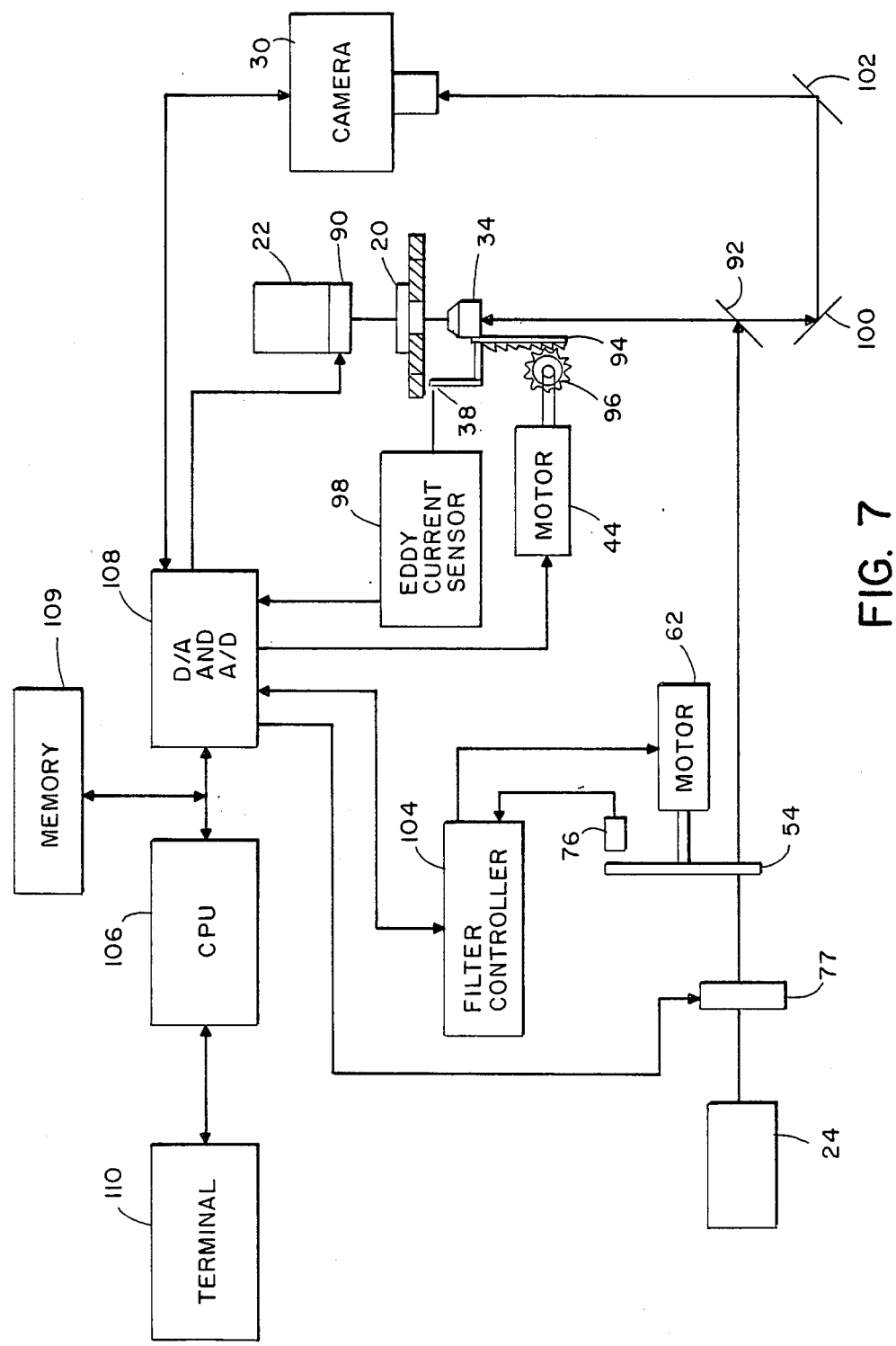

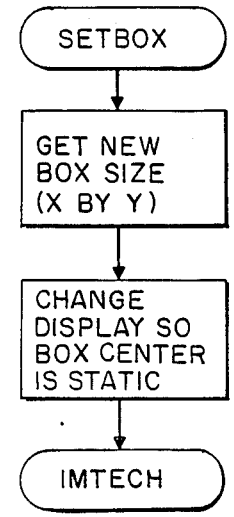
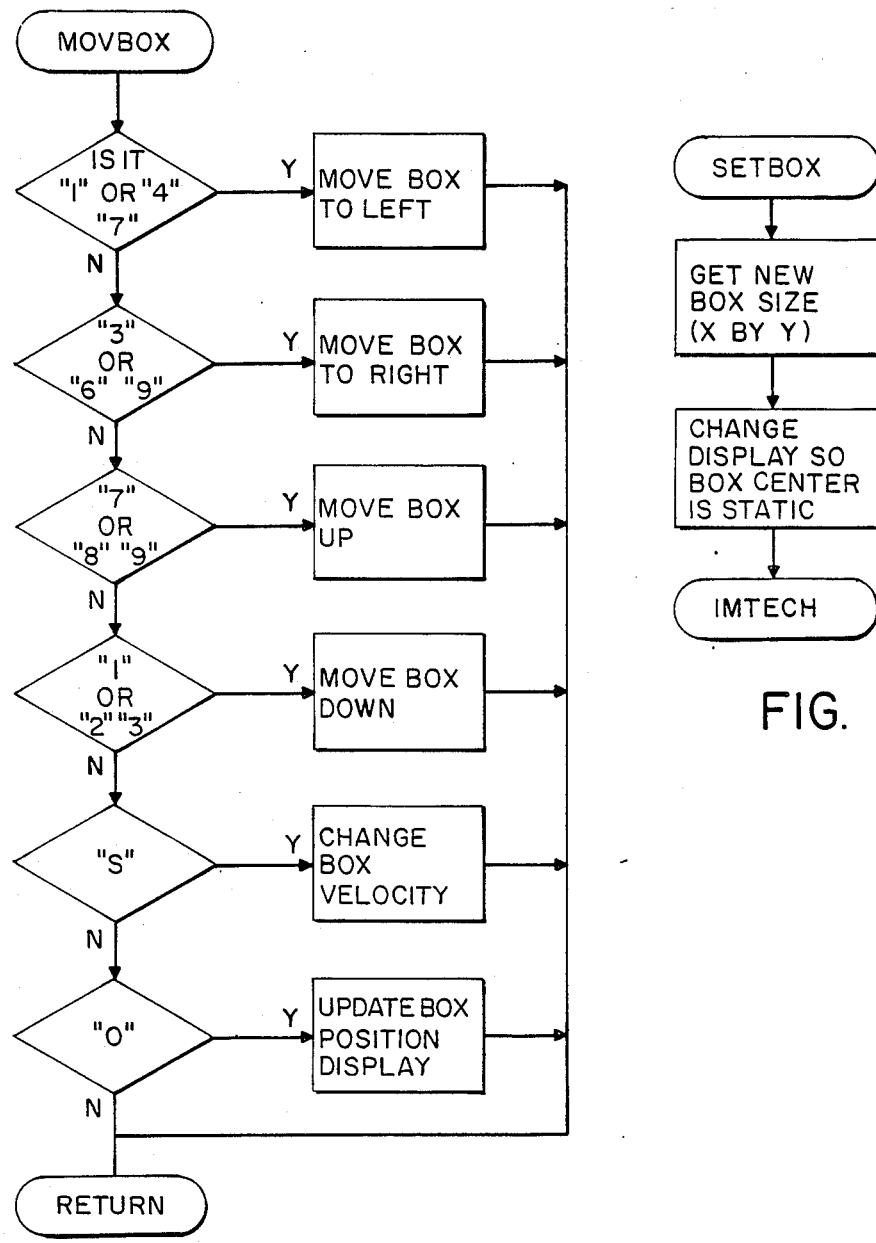
FIG. 8C
FIG. 8D

IMAGING MICROSPECTROFLUORIMETER

DESCRIPTION

This is a continuation of co-pending application Ser. No. 034,777 filed on Apr. 3, 1987, now abandoned, which is a continuation-in-part of application Ser. No. 900,407, filed Aug. 26, 1986 and entitled "Microspectrofluorimeter," now U.S. Pat. No. 4,744,667, which is a continuation-in-part of Ser. No. 828,766, filed Feb. 11, 1986, now abandoned.

1. Related Publication

Details of this invention are presented in "Analysis of Molecular Distribution in Single Cells Using a Digital Microscope," *Optical Methods in Cell Physiology*, DeWeer and Salzburg, eds., 1986, which is incorporated herein by reference.

2. Background

In scientific research, a material can often be characterized by the response of a fluorescent probe to radiation. In some procedures, a sample is illuminated alternately with light of different wavelengths and the fluorescence of the sample with the different illuminating wavelengths is noted. For example, the calcium ion is believed to control a variety of cellular processes with a high degree of spatial and temporal precision. Calcium has been measured in single living cells with high spatial resolution utilizing a microscope and a highly fluorescent calcium sensitive dye Fura-2. A sample to which the dye has been added is illuminated alternately with light of 340 and 380 nanometers. The free fluorescent dye fluoresces at about 500 nanometers maximally in response to the 380 nanometer excitation; whereas, the dye associated with the calcium ion fluoresces at about 500 nanometers maximally in response to the 340 nanometer excitation. The concentration of calcium can then be calculated from the formula:

$$[Ca^{++}]_i = K_d[(R - R_{min})/(R_{max} - R)]\beta$$

Where $K_d$ is the effective dissociation constant for the Fura-2-Calcium reaction, R is the ratio of fluorescent intensity at 500 nm with the 340 and 380 nm excitation, $R_{min}$ is the limiting value of R at a calcium concentration of zero, $R_{max}$ is R with fully saturated calcium and $\beta$ is an optical constant for the system which is a measure of the relative quantum yield at 380 nm of the calcium free and calcium saturated dye.

Often, the distribution of the fluorescent probe or the ratio of the distribution of the probe in its free form relative to its distribution in a bound form within a sample is of interest. For example, the concentration of calcium ions is found to be greater in the cell nucleus than in the cytoplasm. The locations of the ion concentrations have been determined by taking successive two-dimensional images of a sample through incremental focal planes.

The orientation as well as the location of microscopic material may also be significant. For example, alpha-actinin has been observed in muscle cells using fluorescently labeled antibodies specific to alpha-actinin. The location and orientation of the oblong-shaped bodies can be determined by observing the images from plural sections of a sample.

SUMMARY OF THE INVENTION

A microscope is adapted as a microspectrofluorimeter. A filter assembly is positioned in an optical path which includes a source of illumination, a sample on the microscope and a detector. The filter assembly includes a plurality of bandpass filters having different pass bands which are circumferentially spaced about a filter axis offset from the optical path. The filters are driven about the filter axis to move different filter elements into the optical path and thus change the wavelengths of light passing through the filter assembly. A detector such as a video camera detects light from a microscopic portion of the sample. The filter assembly may be positioned between the source of illumination and the sample in order to sequentially change the wavelengths of the illuminating light. Alternatively, it may be positioned between the sample and the detector to detect different frequencies emitted from the sample.

Preferably, the filter is moved under control of an electronic processor to sequentially position predetermined ones of the filters in the optical path of the microscope for sequential measurements using filters of different wavelengths. To insure proper positioning of each filter, a distinctive marking may be provided on the filter disc for each filter to allow the filters to be identified electronically.

Preferably, the image plane of the detector can be controlled by the same microprocessor. Such control is facilitated by position feedback from a sensor which senses the relative positions of a sample and a microscope lens. The system can thus provide plural images using different filters at each of plural specimen planes.

A conventional microscope with a light detector can be quickly converted to a microspectrofluorimeter by means of an accessory which connects quickly between a conventional light source and the microscope or between the microscope and the light detector. The accessory includes an optical conduit between a light inlet and a light outlet. An inlet connector at the inlet end of the optical conduit mates with the conventional microscope light source or the microscope. An outlet connector at the outlet end of the optical conduit mates with the microscope or the detector.

A filter assembly is eccentrically mounted relative to the optical conduit. It includes a filter housing and a filter disc within the housing. The filter disc has a plurality of filters circumferentially spaced about a filter axis offset from the optical conduit. Each filter may be removably attached to the filter disc. The accessory includes a drive motor for rotating the filters about the filter axis. To make the accessory adapted to a wide range of microscopes, the inlet and outlet connectors are identical to the pinned bayonet connectors typically found between light sources and microscopes.

BRIEF DESCRIPTION OF THE DRAWINGS

The foregoing and other objects, features, and advantages of the invention will be apparent from the following more particular description of a preferred embodiment of the invention, as illustrated in the accompanying drawings in which like reference characters refer to the same parts throughout the different views. The drawings are not necessarily to scale, emphasis instead being placed upon illustrating the principles of the invention.

FIG. 7 is a schematic illustration of the system;

DESCRIPTION OF A PREFERRED EMBODIMENT

Figure 1:
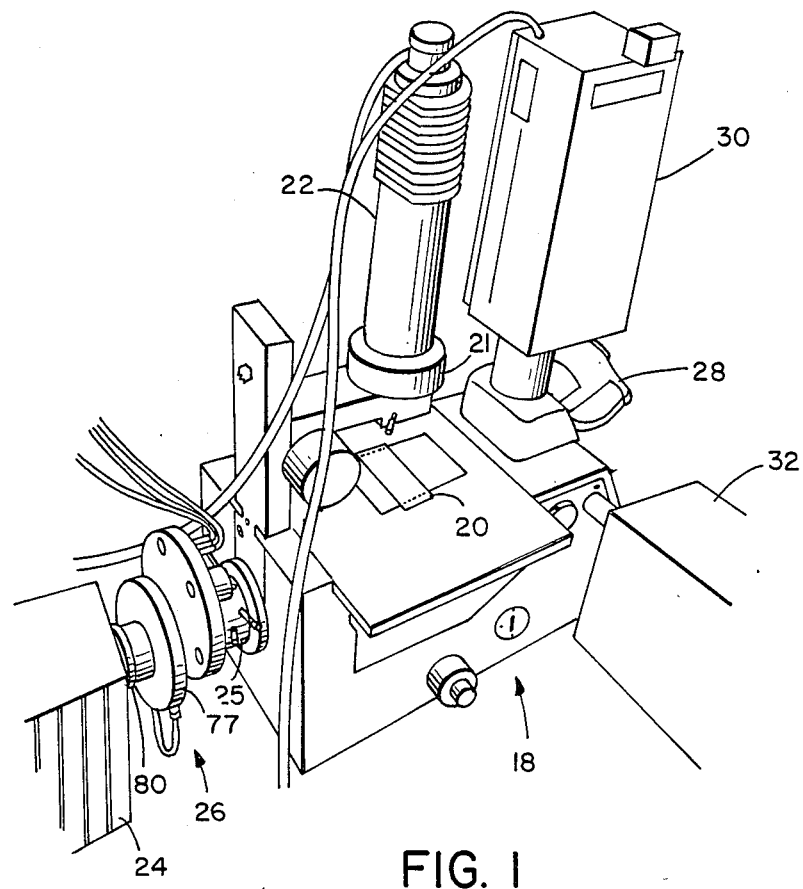
FIG. 1 is a perspective view of a microspectrofluorimeter embodying the present invention.

A conventional microscope 18 modified in accordance with the present invention is illustrated in FIG. 1. A sample slide is shown at 20. The sample may be illuminated from above by a light source 22 through a shutter 21. Alternatively, a sample may be illuminated from a xenon arc lamp 24 which would typically be connected directly to the microscope at 25. In accordance with the present invention, however, a filter assembly 26 is positioned in the optical path between the light source 24 and the sample 20.

Using either light source, the specimen can be viewed through a binocular viewer 28, and an output spatially resolved in two dimensions can be provided by an electronic camera 30 which may be of the vidicon or CCD type. To provide a quantitative indication of the fluorescence from a sample at high time resolution, a photomultiplier tube 32 may be coupled to the system.

Figure 2:
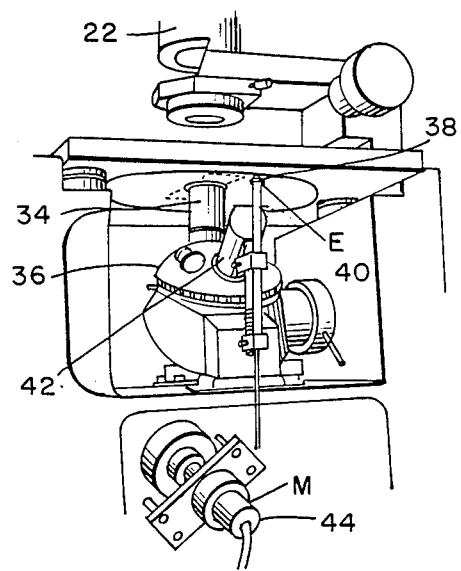
FIG. 2 is a partial perspective view of the microspectrofluorimeter of FIG. 1 as viewed from the rear.

The focusing mechanism of the microscope is illustrated in FIG. 2 which is a view from the rear of FIG. 1. A number of alternative lens assemblies such as at 34 may be mounted to a turret 36. However, the present system is modified to mount an eddy current position sensor at one of the lens sockets. The eddy current sensor 38 is mounted at the top of a tube 40 which is adjustably mounted to a support 42 mounted to the lens turret. For focusing, the lens turret is typically moved up and down relative to the sample under manual control. However, with the present system, the up and down movement of the turret may be controlled by a stepper motor 44 upon locking of the motor onto the drive shaft of the focus mechanism. The plane within the specimen from which an image is taken can thus be varied through a range of image planes.

Figure 3:
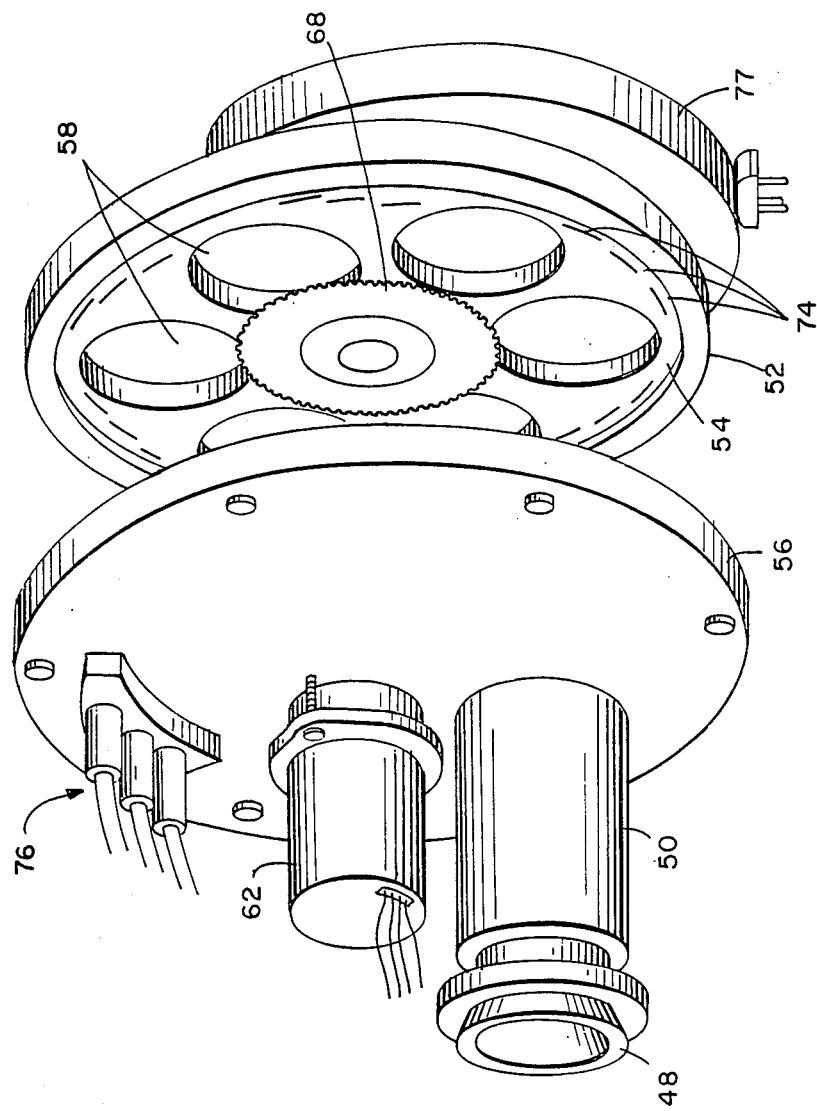
FIG. 3 is an exploded perspective view of the filter assembly of FIG. 1 as viewed from the rear.
Figure 4:
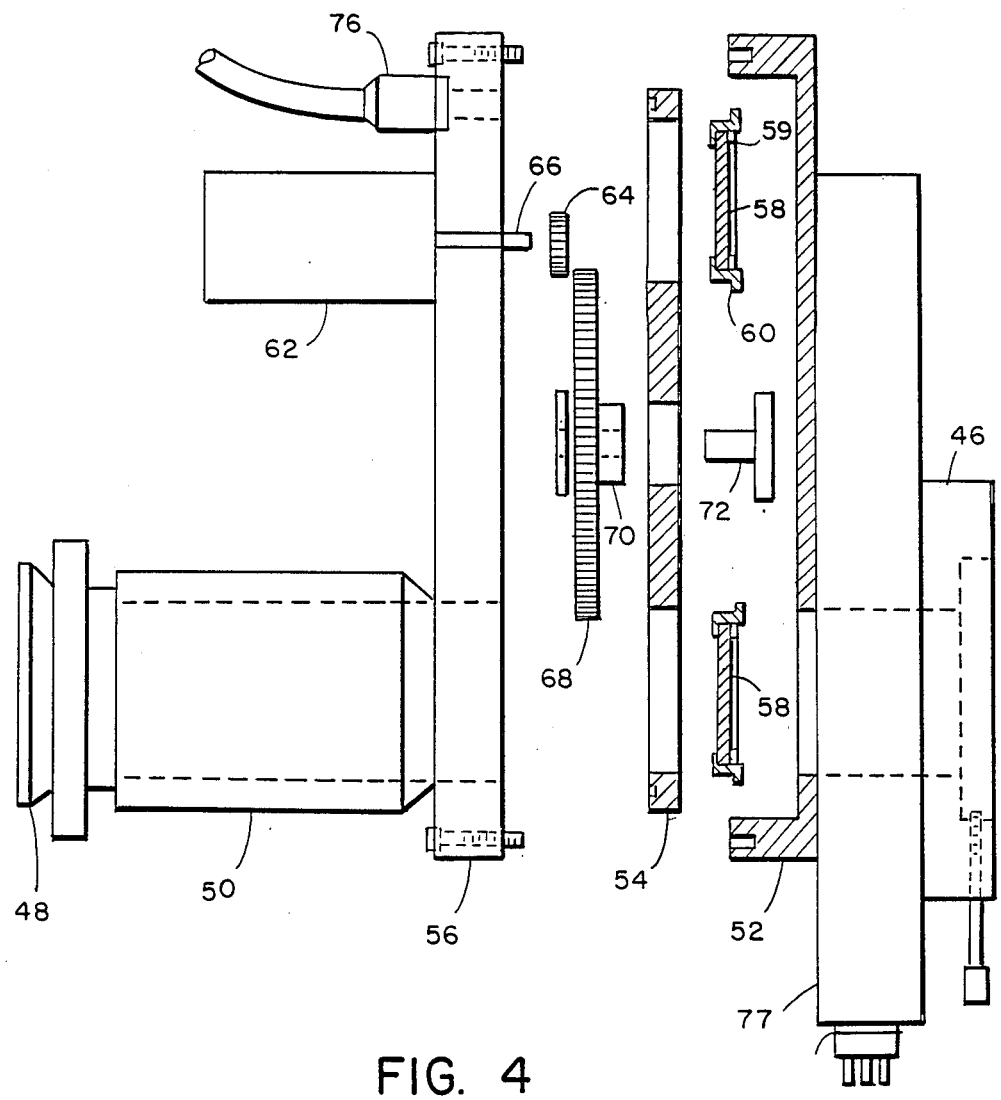
FIG. 4 is an exploded side view of the filter assembly of FIG. 3.
Figure 5:
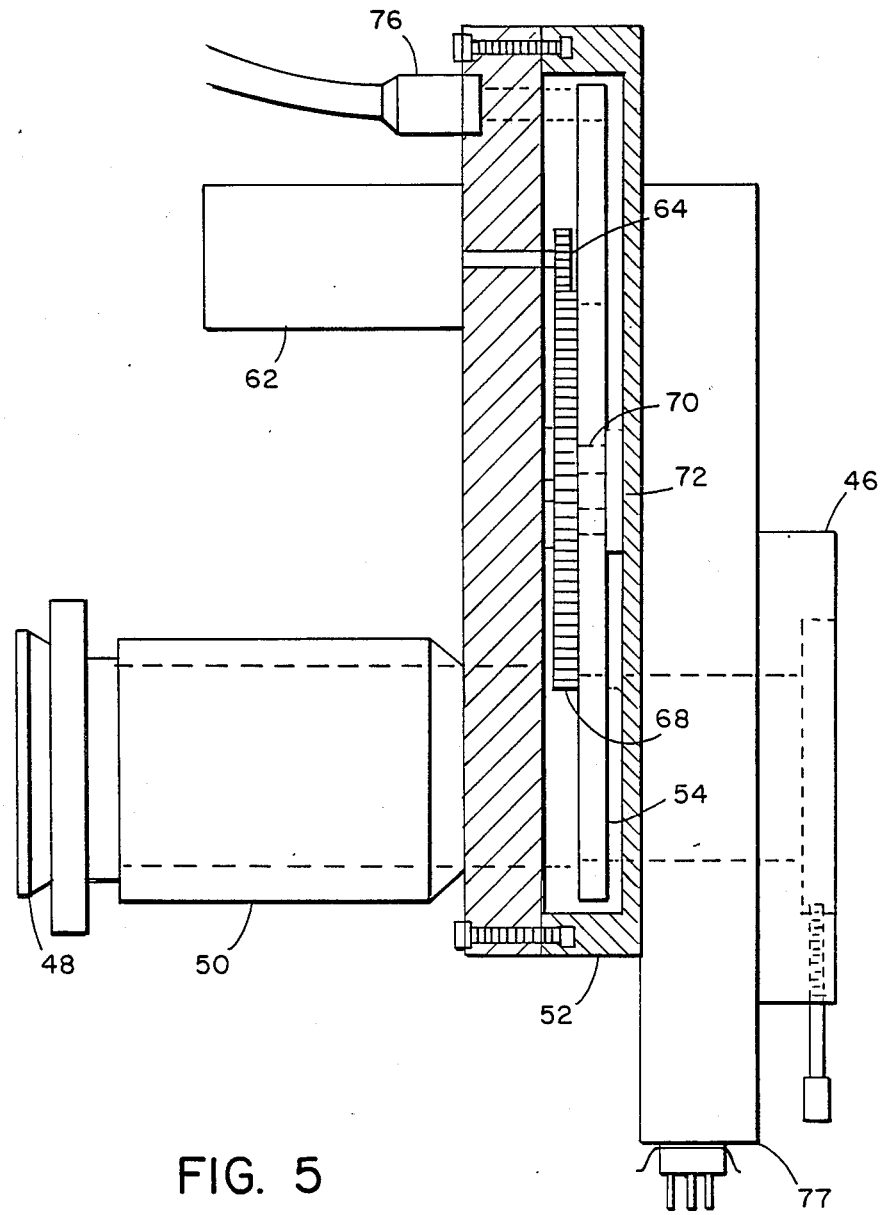
FIG. 5 is a side view, partially in section, of the filter assembly of FIG. 3.

Enlarged views of the filter accessory 26 are shown in FIGS. 3 through 5. The accessory includes the female portion 46 or a connector for coupling the accessory to the xenon arc lamp 24. The accessory also includes a male portion 48 of a connector for connecting it to the microscope 18. A beam of light from the light source 24 is transmitted through an optical conduit 50 between the connectors. A filter housing 52 having a coverplate 56 is eccentrically mounted to the optical conduit. It houses a filter disc 54 which carries a plurality of filter elements 58. Each filter is retained in a carrier 60 by a circular spring clip 59 as shown in FIG. 4. Each carrier 60 is removably inserted into a hole in the disc. The filter is retained in the hole by a spring biased detent, not shown. One opening in the disc may be left open for transmission of white light.

The filter disc may be rotated to selectively position filters in the optic path through the conduit 50. The disc is rotated by means of a stepper motor 62 mounted to the coverplate 56. A gear 64 mounted to the motor drive shaft 66 drives a second gear 68 mounted to the filter disc. The hub 70 of the gear 68 is press fit into the center hole in the disc. The hub 70 rotates about a shaft 72 which is mounted to the rear surface of the housing 52.

To precisely determine that a filter is positioned in the optic axis of the system and to identify that filter, a set of three optically coded marks 74 is associated with each filter. The marks are staggered both circumferentially and radially and are detected by a set of three photodetectors 76.

An electrically controlled shutter 77 is positioned in the optic path between the connector 46 and the filter housing 52.

Figure 6:
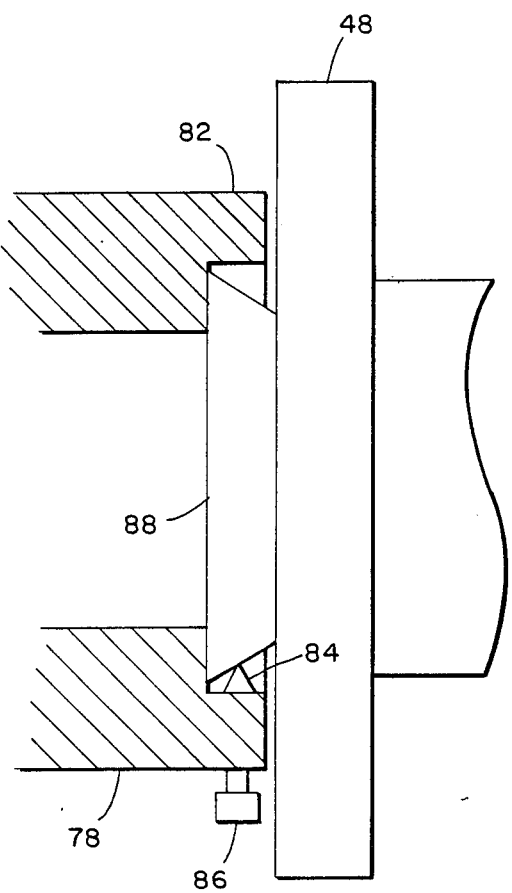
FIG. 6 is a side view, partially in section, of a pinned bayonet connector.

In order that the filter accessory can be readily mounted between a conventional microscope and its conventional light source, bayonet optical connectors 46 and 48, as illustrated in FIG. 6, are provided. FIG. 6 shows the female portion 78 of the connector typically found on a microscope and the male portion 48 on the accessory. The connector 80 on the xenon arc lamp would be substantially the same as the connector 48, and the connector 46 of the accessory would be functionally the same as connector 78 on the microscope housing.

The female portion of the connector includes two fixed pins (not shown) which extend radially inward from the rim 82 of the connector socket. A third pin 84 is spring biased so that it can be pulled outward by a pinhead 86. With the pin 84 thus pulled away from the socket, the frustoconical male portion 88 of the connector on the accessory can be slipped behind the two fixed pins. When the pin 84 is then released, the pin 84 presses against the conical surface to bring the male portion tightly into the socket. The pin can then be locked into place by manipulating the head 86.

FIG. 7 is a schematic illustration of the system. As already discussed, a sample at 20 may be illuminated from above by a light source 22 which may be associated with a shutter 90. Alternatively, the sample may be illuminated from below by means of a light source 24. The light from the light source 24 is directed through the shutter 77 and the filter disc 54 and is reflected upward by a light splitter 92. The objective lens assembly 34 may be moved up and down for focusing by a rack 94 and pinion 96. The pinion 96 is driven by the stepper motor 44. To precisely monitor the position of the lens 34 relative to the sample 20, an eddy current sensor 38 is mounted to the lens assembly and connected to eddy current sensor electronics 98.

Light from the sample is returned through the lens 34 and the dichroic mirror 92 and is directed to the camera 30 by mirrors 100 and 102. A typical microscope includes additional optics in the light path to the camera, but such are conventional and are not shown here.

A filter controller 104 is provided to monitor the outputs of the photodetectors 76 and to drive the stepper motor 62. The filter controller has sufficient logic to respond to either a manual or electrical input designating one of the six filters, to determine the present position of the filter disc, to determine the shortest path to the desired filter and to drive the motor 62 in the proper direction. The controller also responds to the outputs of the photodetectors 76 to stop the motor when the designated filter is properly positioned. It then returns an acknowledgement signal to the CPU 106.

The entire system is controlled by central processing unit 106 through digital to analog converters of converter unit 108. The CPU 106 controls the shutter 77, the shutter 90, and the focusing motor 44 and, through the filter controller 104, it controls the filter motor 62. The CPU receives an acknowledge signal from the filter controller when a selected filter is positioned in the optic path and receives position input from the eddy current sensor electronics 98 through an analog to digital converter of converter unit 108. Under control of the cpu, signals from the camera 30 are received through the analog to digital converters of unit 108 and are stored in the memory 109 for processing. A user may control the data collection and display at a terminal 110.

Figure 8A:
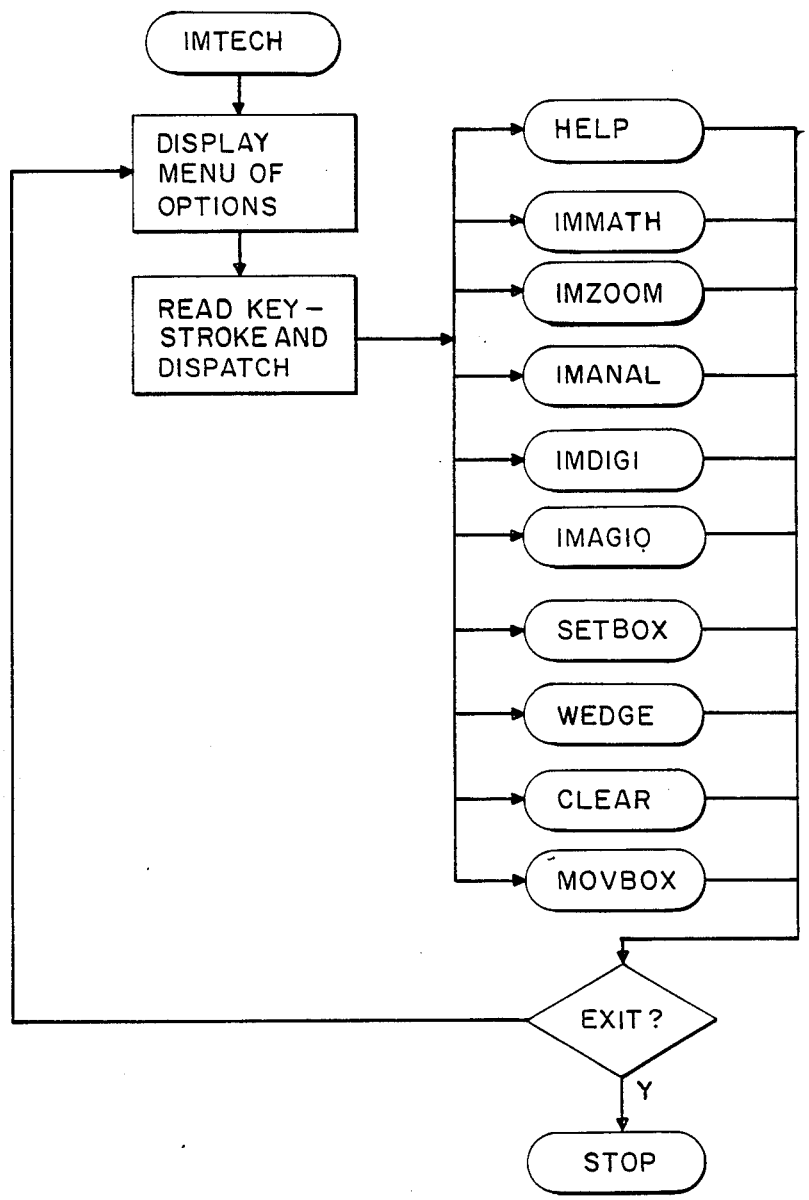
FIGS. 8A—8O are block diagrams of the system software.
Figure 8B:
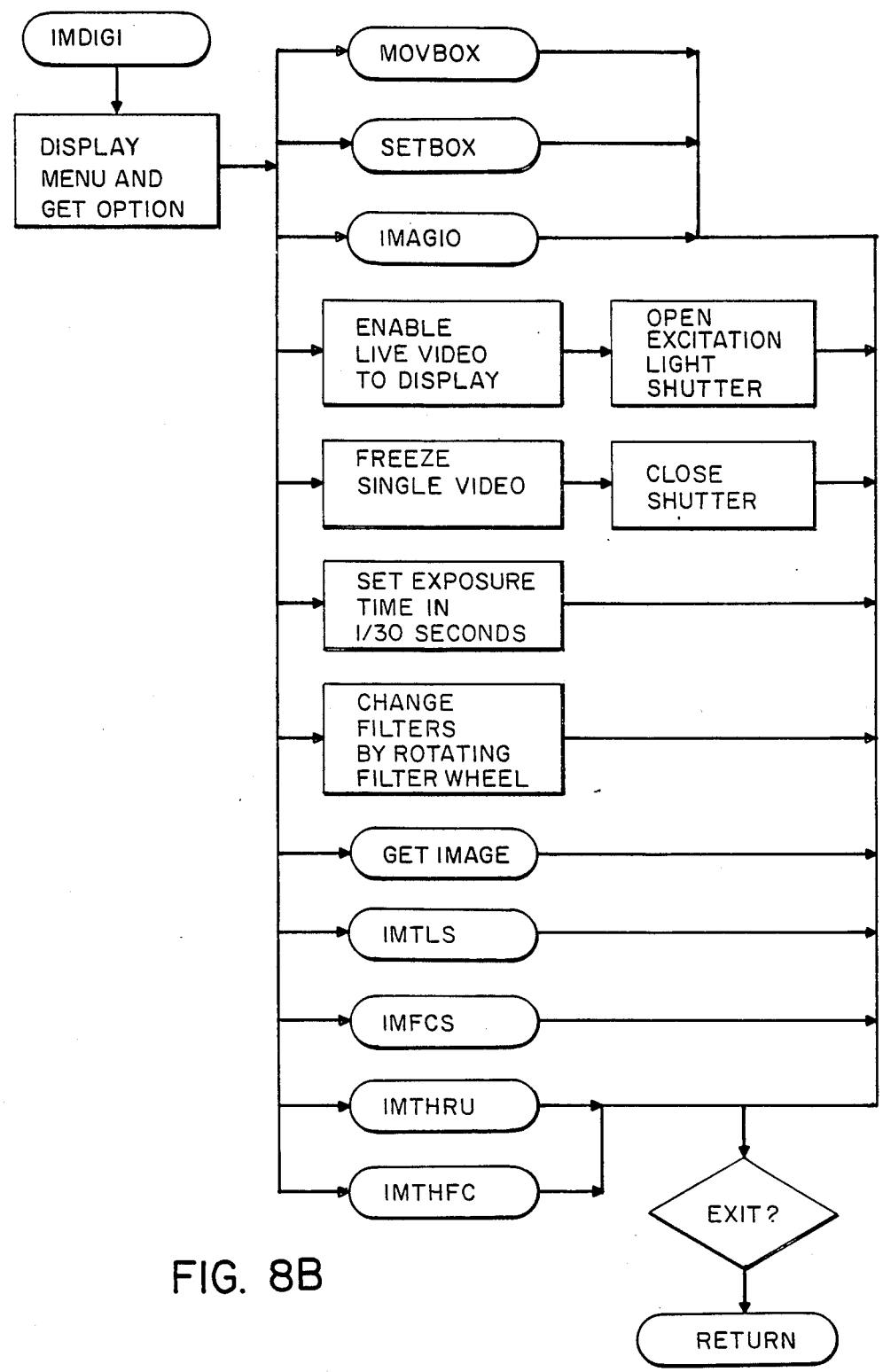
Figure 8E:
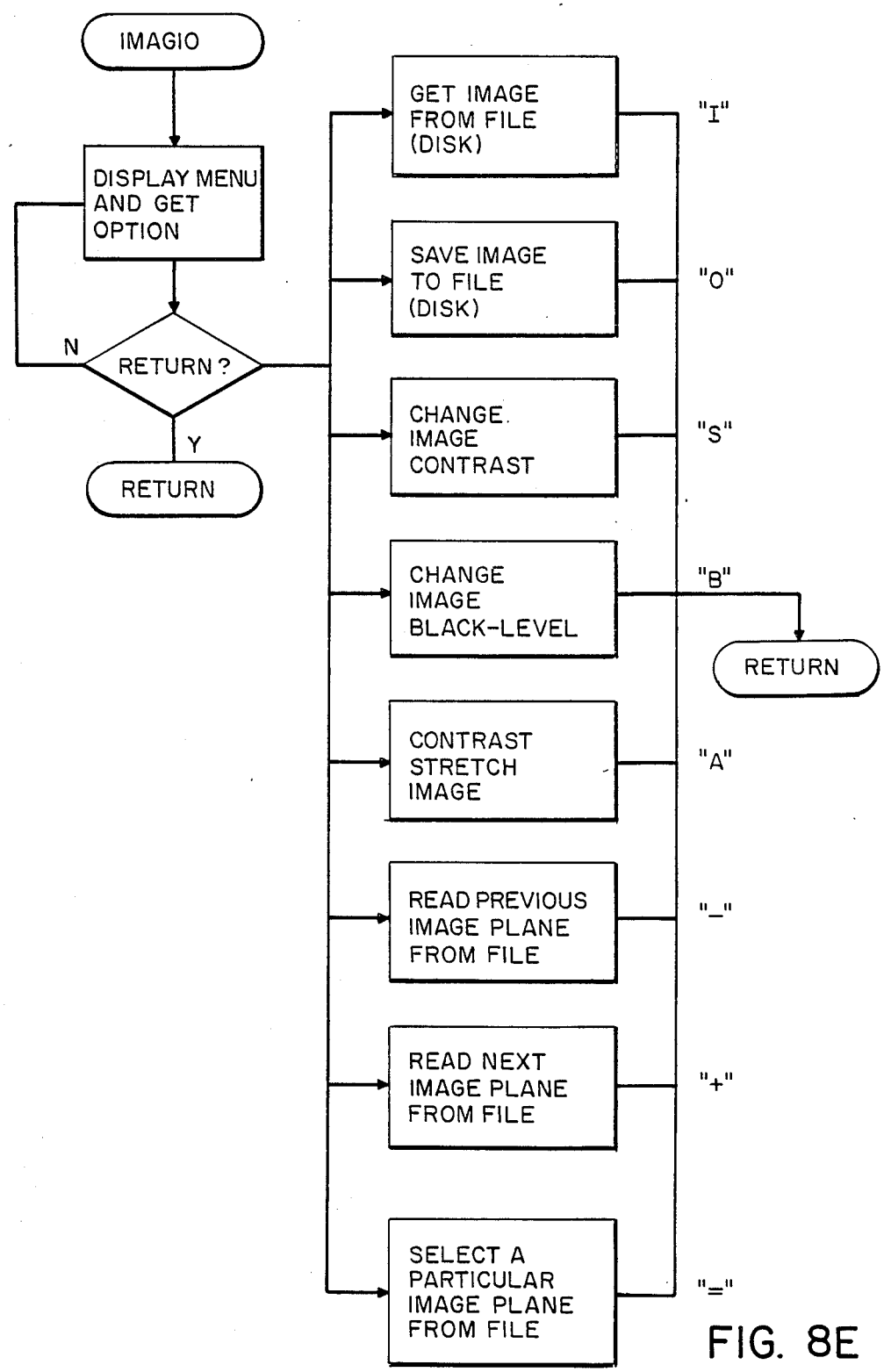

The software for controlling the system is illustrated in FIGS. 8A through 8O. As illustrated in FIG. 8A, a number of routines may be selected by keyboard input after viewing a menu display. Image digitization and microscope control is handled by the routine IMDIGI of FIG. 8B. Again, various subroutines may be selected by keystroke after viewing a display menu. The SETBOX subroutine is illustrated in FIG. 8C. By this subroutine a window of interest in an image may be established. Then, by the MOVBOX of FIG. 8D, the box may be moved to the location of interest. Thereafter, image storage and processing may be limited to the window of interest. The subroutine IMAGIO allows for image input to and from disc files. It also allows for such tasks as contrast and black level control. As illustrated in FIG. 8B, the routine IMDIGI also allows for viewing of the video display with the light shutter open even though images are not stored, and it allows a single video frame to be retained and viewed after the shutter is closed. This latter function allows the user to designate a region of interest using the SETBOX and MOVBOX routines without continued illumination of the sample. Illumination of the specimen can thus be carefully controlled to minimize bleaching of the fluorescent probes and possible light induced changes in cell function due to prolonged exposure to a strong light source. The routine IMDIGI also allows for setting of the exposure time and for direct selection of a particular filter of the filter disc.

Figure 8F:
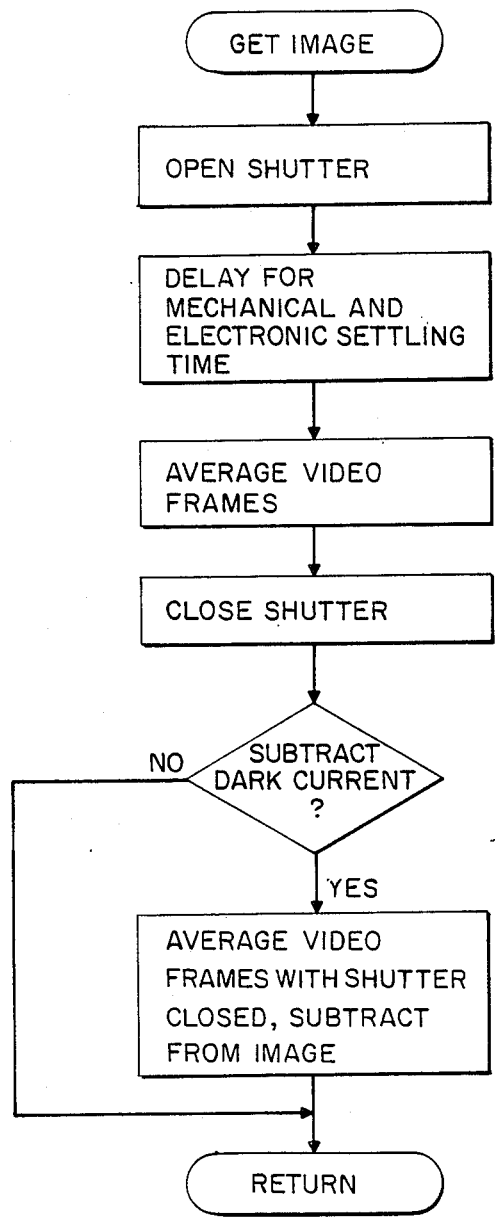
Figure 8G:
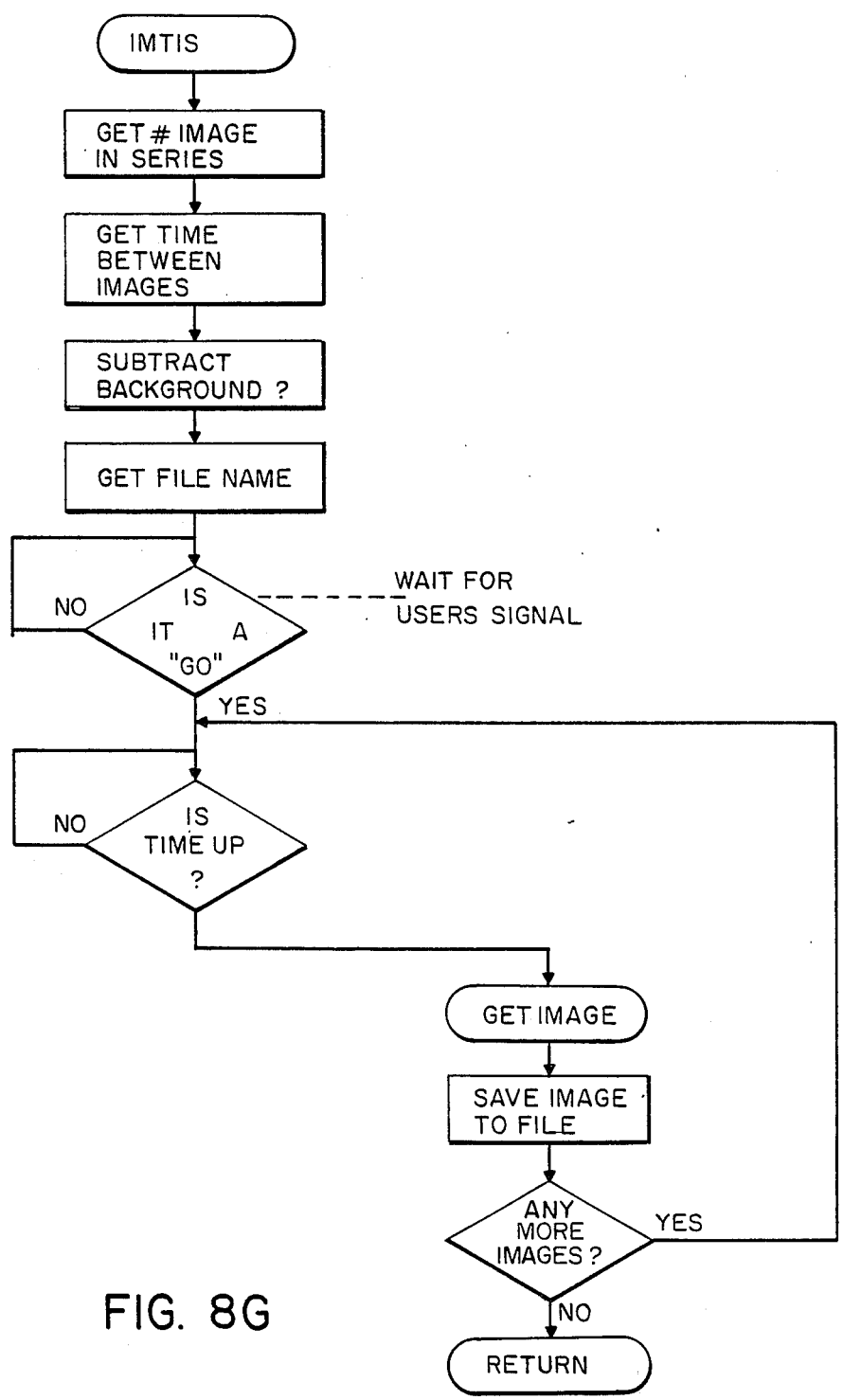
Figure 8H:
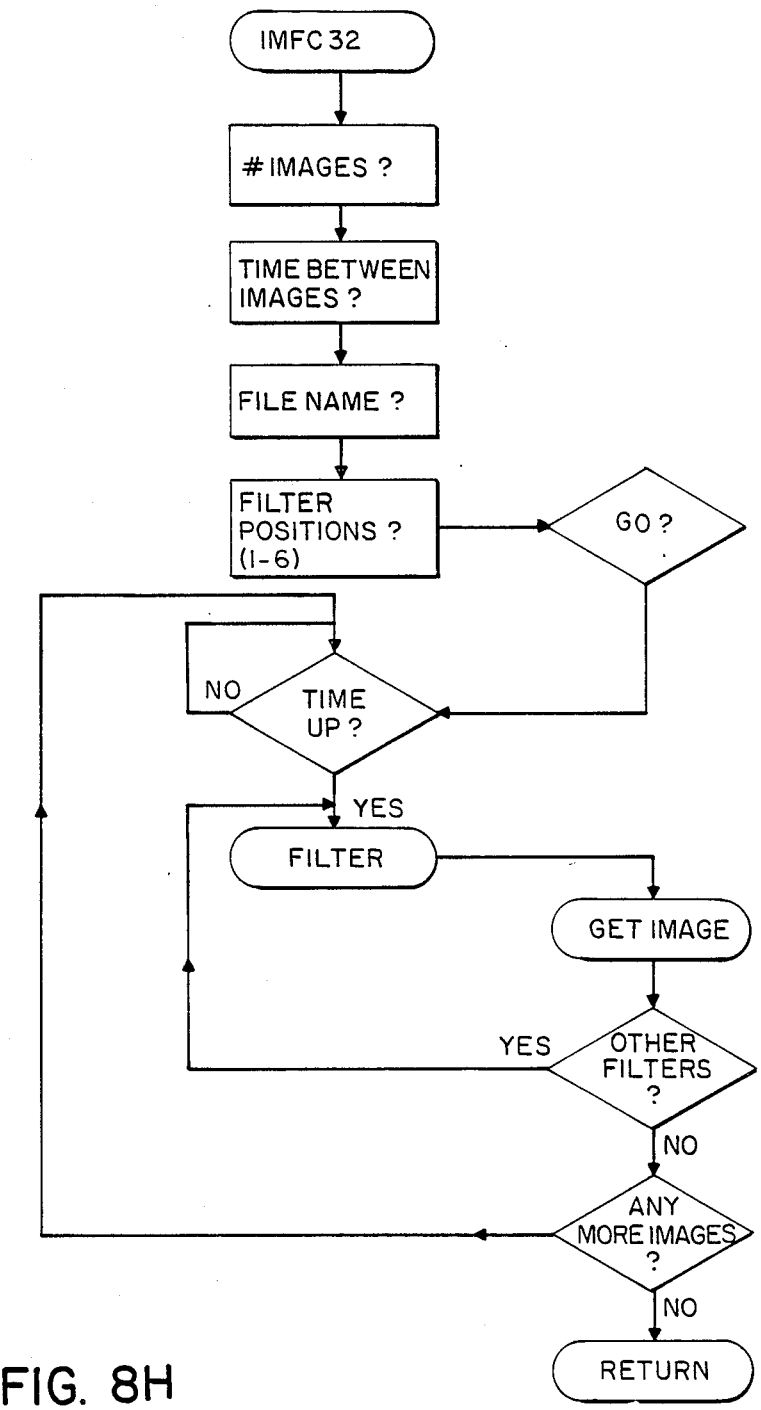

The IMDIGI routine allows the storage of a single image through the GETIMAGE subroutine of FIG. 8F. After the shutter is opened, a delay is allowed for mechanical and electronic settling of the system before collection of data. In order to reduce the contribution of noise to the image, successive video frames at the system frame rate of 30 frames per second are summed. The user may select the number of frames which are summed. It is then the summed frame rather than an individual frame which is retained for further processing. Further, the subroutine allows for the summing of the video signal with the shutter closed and allows that summed image to be subtracted from the image with the shutter open. Subtraction of that image reduces the contribution of noise that is spatially variant but constant in time such as that due to spatial variations in dark current in the camera.

The routine IMDIGI also allows for automatic imaging of a sample sequentially over time, with different filters, and through different focal planes.

Figure 8I:
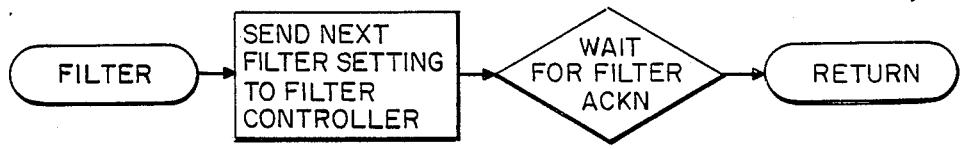

The IMTLS routine allows the user to obtain a series of images spaced by set increments in time. The IMFCS routine similarly allows for time lapse imaging and further allows the system to obtain images using each of several filters at each increment of time. To that end, a FILTER subroutine of FIG. 8I is called. The FILTER subroutine sends a signal to the filter controller 104 indicating the number of the selected filter. The filter controller moves the filter disc to the selected filter and then acknowledges completion of the chore to the CPU.

Figure 8K:
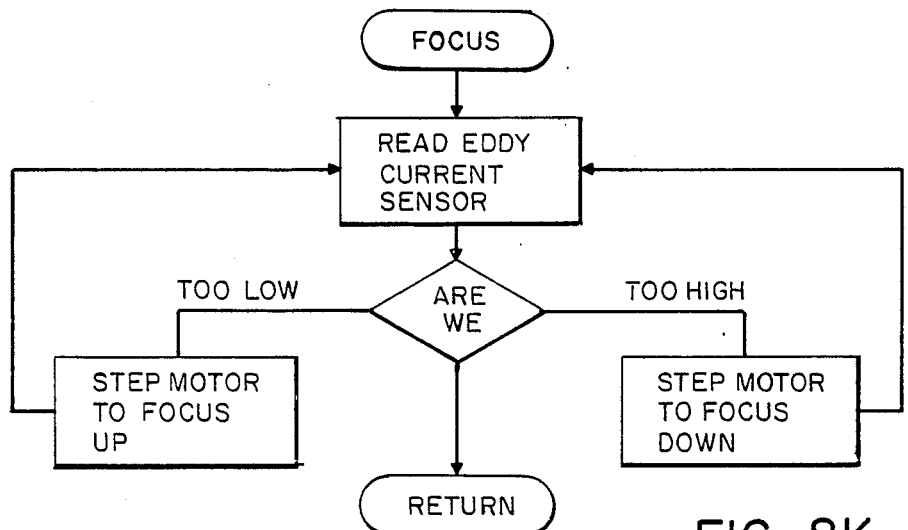
Figure 8M:
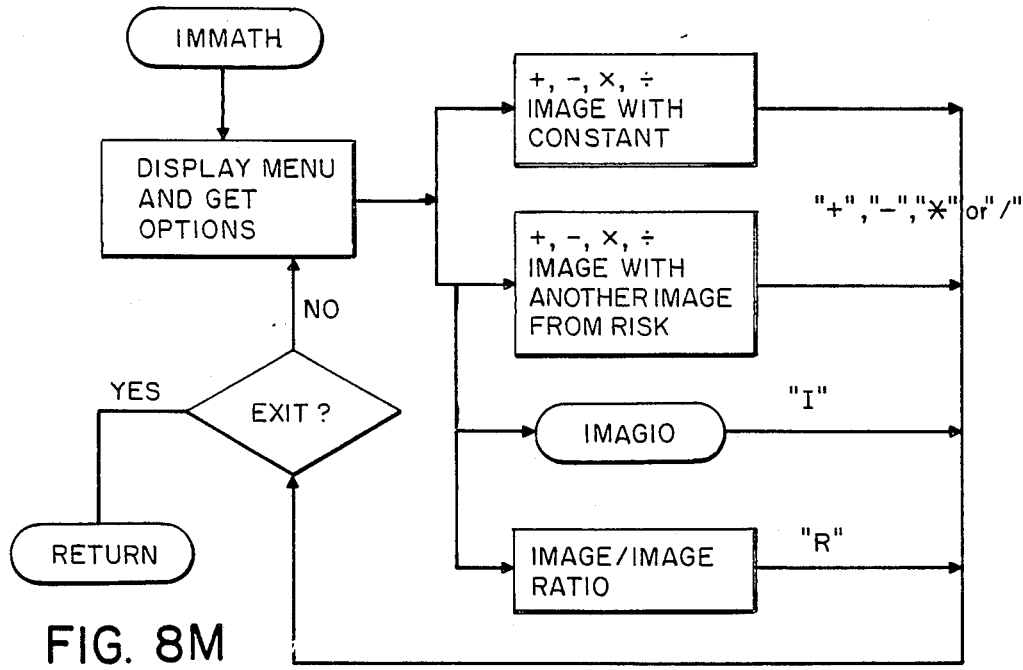
Figure 8J:
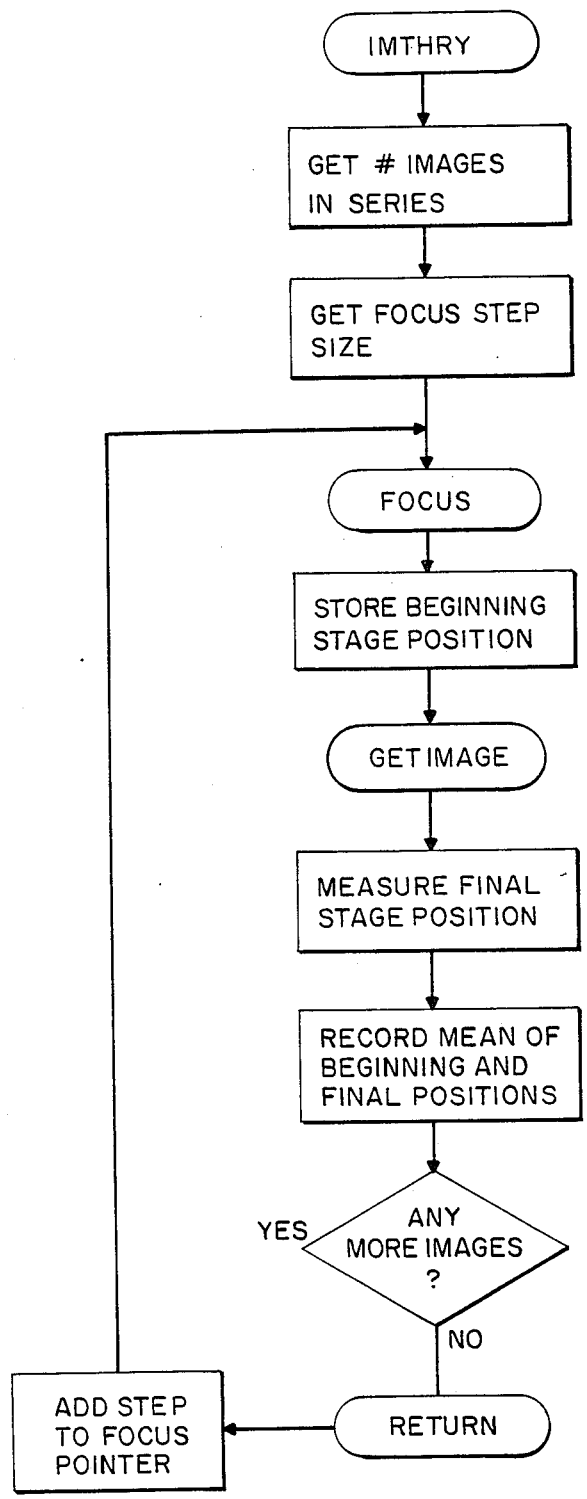
Figure 8L:
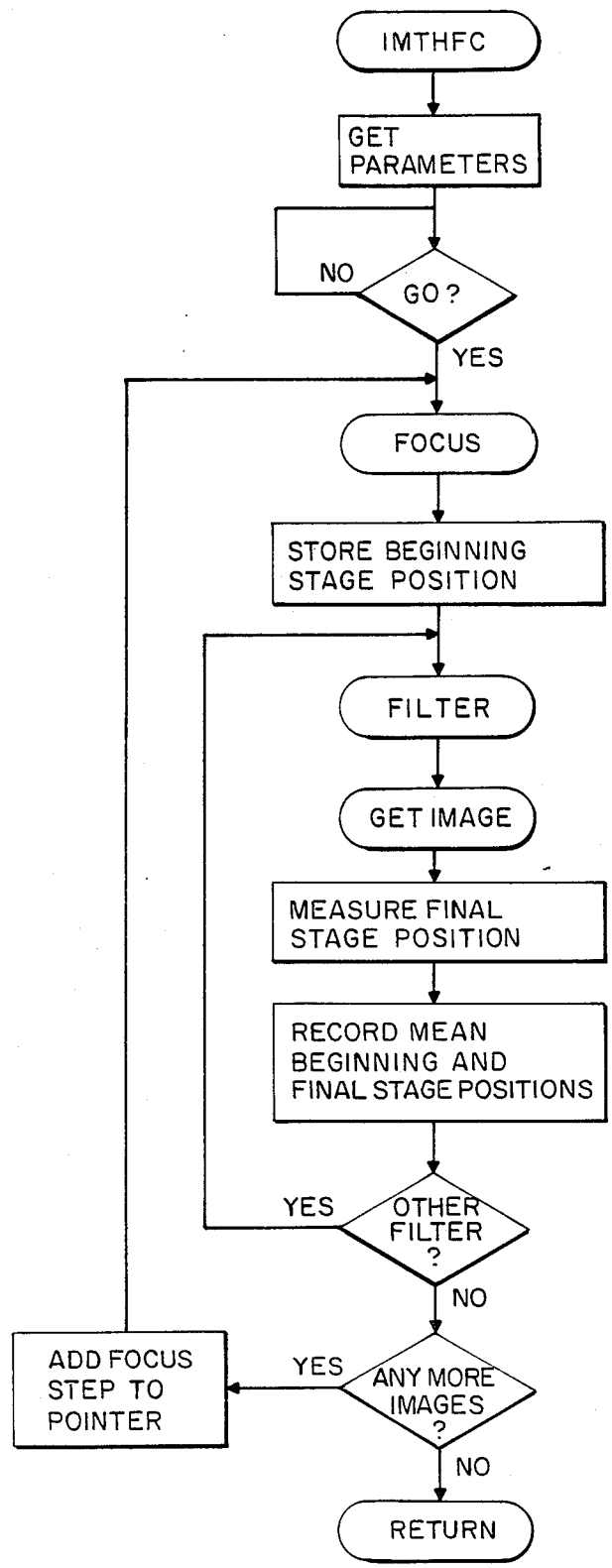

The IMTHRU routine of FIG. 8J generates a sequence of images at incrementally spaced image planes within the sample. This routine relies on the subroutine FOCUS of FIG. 8K. In that subroutine, the output of the eddy current sensor 98 is detected and the motor 44 is driven to precisely set the image plane. Because there may be some small drift in position during the imaging procedure, the position is detected both before and after imaging and the mean is stored with the recorded message.

The final image collection routine available through IMDIGI is the IMTHFC routine. By this routine, multiple focal planes may be imaged, and multiple filters may be used at each focal plane.

The main routine of FIG. 8A also allows selection of the IMMATH routine of FIG. 8M. This routine allows individual pixels of each image to be operated on by a constant or the pixel of another image from storage.

Figure 8N:
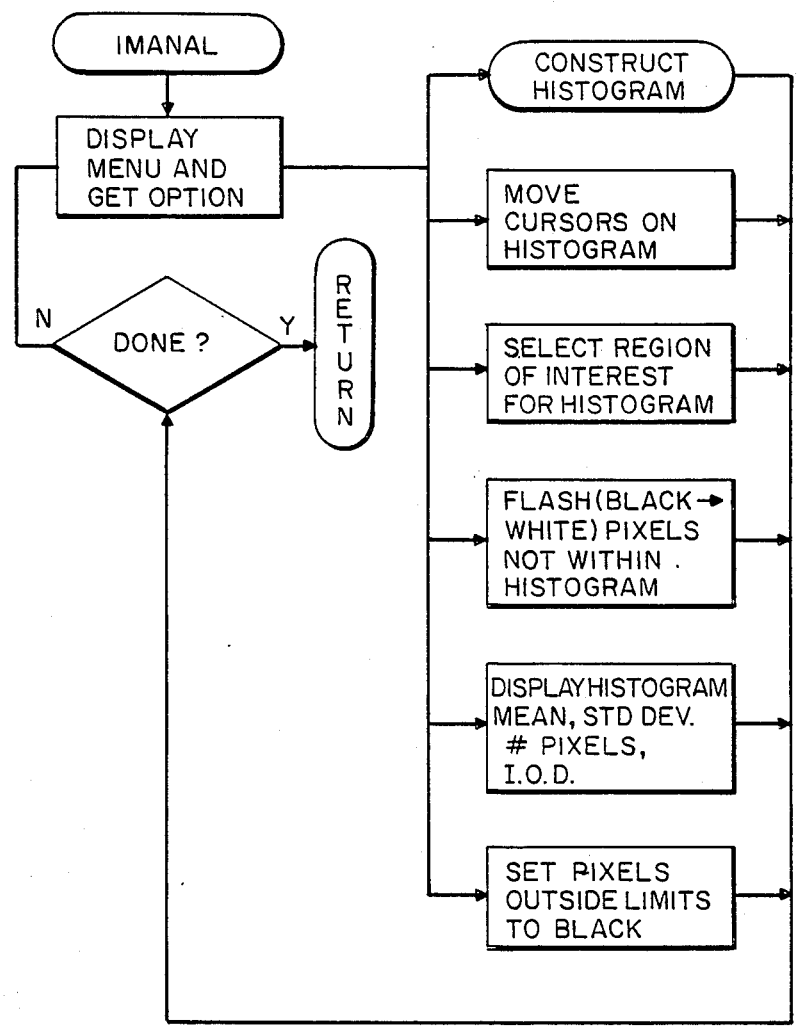
Figure 80:
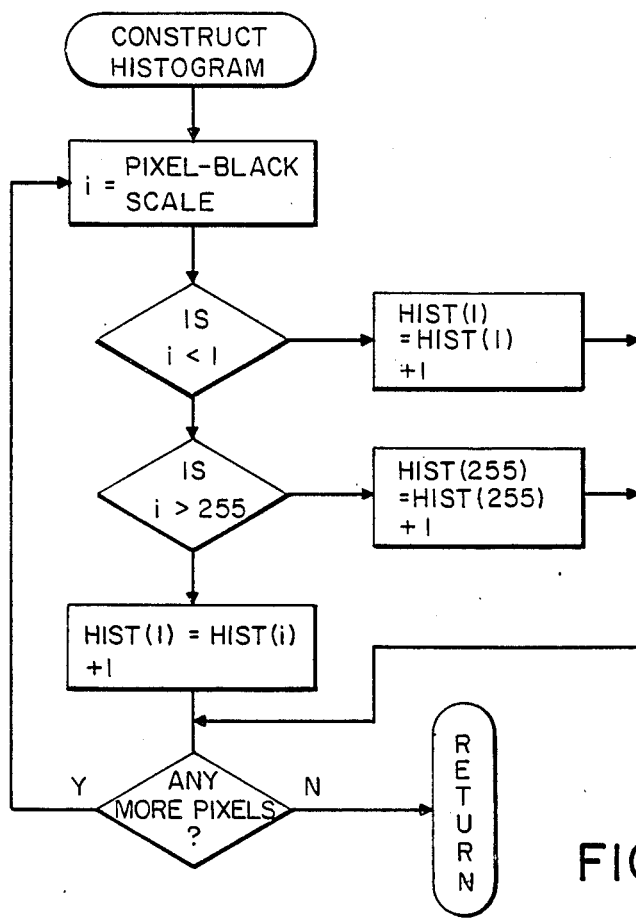
Figure 9:
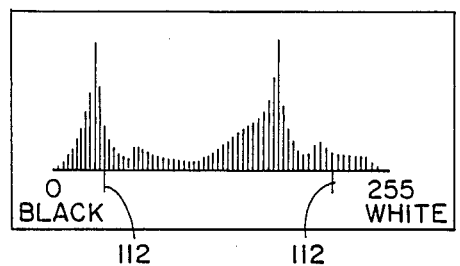
FIG. 9 is an illustration of a histogram which might be generated on the system display.

The IMANAL routine available through IMTECH is illustrated in FIG. 8N. This routine allows for the construction of histograms as illustrated in FIG. 9. Through the CONSTRUCT HISTOGRAM subroutine of FIG. 8O, the number of pixels in an image having each of the possible 256 intensity levels is determined. That number of pixels is then displayed as a percentage of the total number of pixels. A viewer can then examine that histogram and isolate a particular range of intensities of interest by movement of cursors 112. Those pixels outside the range indicated by the cursors may then be set to the black level and thus be excluded from the display. The user can then view the recreated image and make adjustments to the cursors to obtain the desired image. IMANAL also allows for the computation of several descriptive outputs with respect to the original image and with respect to the images selected through the histogram. Specifically, the mean gray level, its standard deviation, the integrated light intensity and the total number of pixels may be calculated for each image.

The above-described system allows for great flexibility for making precise measurements of microscopic sample. The plural filters allow for the successive measurements required to, for example, determine the concentration of calcium ions. The multiple filters also allow for a single filter setup to be used for different analyses at a laboratory. In combination with the automatic control of the focal plane, the filter selection allows for the rapid collection of complex data.

While this invention has been particularly shown and described with references to preferred embodiments thereof, it will be understood by those skilled in the art that various changes in form and details may be made therein without departing from the spirit and scope of the invention as defined by the appended claims. For example, although the filter accessory has been shown positioned between the light source and microscope, for some tests it might be more appropriately positioned between the microscope and the camera. Also, the filters need not be color filters; other optical characteristics may be filtered depending on application requirements.

We claim:
1. A microscope comprising:
means for locating a sample;
a source of radiation for illuminating the sample;
a detector for detecting radiation from a microscopic portion of the sample;
a filter assembly in an optical path between the source and the detector, the filter assembly comprising a plurality of removable bandpass filters having different pass bands mounted to a filter carrier and circumferentially spaced about a filter axis offset from said optical path and filter drive means for rotating the filter carrier about the filter axis to selectively move selected ones of the plurality of filters into said optical path to change the wavelengths of radiation passed through the filter assembly;
means for sensing the position of the filter carrier as each filter is positioned in the optical path; and
electronic processor means for controlling imaging of the sample, the processor automatically controlling the filter drive means to sequentially position predetermined one of the filters in the optical path and sequentially adjusting the image plane of the detector to obtain plural images at different image planes with each of plural filters.

2. A microscope as claimed in claim 1 wherein the detector is a two-dimensional detector.

3. A microscope as claimed in claim 2 wherein the image plane is controlled by driving a lens carrier along its optic axis.

4. A microscope as claimed in claim 1 wherein the filter assembly is a microscope accessory removably mounted to the microscope.

5. A microscope as claimed in claim 4 wherein the drive means is a stepper motor.

6. A microscope as claimed in claim 4 wherein the filter assembly accessory is connected by means of complementary pinned bayonet connectors.

7. A microscope as claimed in claim 4 wherein each of the bandpass filters is a filter element positioned in an element carrier which is removable from the filter carrier.

8. A microscope comprising:
means for locating a sample;
a source of radiation for illuminating the sample;
a two-dimensional detector for detecting images of a microscopic portion of the sample;
a filter assembly in an optical path between the source and the detector, the filter assembly comprising a plurality of bandpass filters having different pass bands circumferentially spaced about a filter axis offset from said optical path;
a filter motor for rotating the filters about the filter axis to selectively move selected ones of the plurality of filter elements into said optical path to change the wavelengths of light passed through the filter assembly;
a focusing motor for adjusting the image plane of the detector in the sample; and
electronic processor means for automatically controlling the focusing motor and the filter motor to obtain plural images using different filters at each of plural focal planes.

9. A microscope as claimed in claim 8 wherein each of the bandpass filters is a filter element positioned in an element carrier which is removable from a filter carrier.

10. A microscope as claimed in claim 8 further comprising means for windowing a region of a displayed image and for limiting processing of the image to the windowed region.

11. A microscope as claimed in claim 8 further comprising a shutter, means for opening the shutter, and means for delaying collection of data relative to the plural images to allow for mechanical and electronic settling after the shutter is opened.

12. A method of measuring the radiation from a sample comprising:
positioning a filter assembly in an optical path between a source of radiation which illuminates the sample and a two-dimensional detector which detects light from the sample, the filter assembly comprising a plurality of bandpass filters having different pass bands circumferentially spaced about a filter axis;
under programmed control, rotating the filters about the filter axis to selectively move filters into the optical path;
sequentially adjusting the image plane of the detector in the sample under programmed control; and
storing detected image from plural image planes with each of plural filters in the optical path.

13. A microscope comprising:
means for locating a sample;
a two-dimensional detector for detecting an image of a microscopic portion of the sample;
a lens movable relative to the sample for focusing a sample image onto the detector;
a focusing motor for adjusting the relative positions of the sample and lens to change the image plane of the detector in the sample;
a sensor for sensing the relative positions of the sample and lens; and
electronic processor means responsive to a control program and the relative position sensed by the sensor means for driving the focusing motor and controlling image detection by the detector to obtain images of the sample at each of the plurality of image planes in the sample.

14. A microscope as claimed in claim 13 further comprising a filter assembly in an optical path between a light source and the detector, the filter assembly comprising a plurality of bandpass filters having different pass bands and being responsive to the control program to selectively position the filters in the optical path.

15. A method of measuring the radiation from a sample comprising:
sensing the relative position from a sample comprising:
sensing the relative position of the sample and a focusing lens;
under programmed control and responsive to the sensed relative positions, sequentially changing the image plane of the detector through the sample; and
storing the detected images form each of the plural image planes.

* * * * *